US 8,055,407 B2

(12) United States Patent
Chiu et al.

(10) Patent No.: US 8,055,407 B2
(45) Date of Patent: Nov. 8, 2011

(54) HEALTH INFORMATION GUIDING SYSTEM AND METHOD THEREOF

(75) Inventors: Chaucer Chiu, Taipei (TW); Hui Fang, Shanghai (CN)

(73) Assignee: Inventec Corporation, Taipei (TW)

( * ) Notice: Subject to any disclaimer, the term of this patent is extended or adjusted under 35 U.S.C. 154(b) by 448 days.

(21) Appl. No.: 12/453,021

(22) Filed: Apr. 28, 2009

(65) Prior Publication Data

US 2010/0274470 A1    Oct. 28, 2010

(30) Foreign Application Priority Data

Mar. 12, 2009 (TW) .............................. 98107974 A

(51) Int. Cl.
*G01C 21/26* (2006.01)
*H04W 4/00* (2009.01)
*G06F 17/00* (2006.01)

(52) U.S. Cl. .............. 701/36; 701/206; 701/211; 705/3; 707/3; 707/102

(58) Field of Classification Search ..................... 701/36, 701/200, 206, 210, 211; 705/2, 3; 707/1, 707/3, 102; 709/217
See application file for complete search history.

(56) References Cited

U.S. PATENT DOCUMENTS

| | | | | |
|---|---|---|---|---|
| 5,867,821 | A * | 2/1999 | Ballantyne et al. | 705/2 |
| 5,960,403 | A * | 9/1999 | Brown | 705/2 |
| 7,786,874 | B2 * | 8/2010 | Rodgers | 340/573.1 |
| 2011/0010087 | A1 * | 1/2011 | Wons et al. | 701/201 |

* cited by examiner

*Primary Examiner* — Tan Q Nguyen
(74) *Attorney, Agent, or Firm* — Bacon & Thomas, PLLC

(57) ABSTRACT

This specification discloses a health information guiding system and the method thereof. By analyzing the user's position information and health data, the invention selects a target location to provide the user with related health and address information. The user is thus able to obtain more complete health information. This increases the value of immediately using the health information.

12 Claims, 5 Drawing Sheets

| Location data | Coordinate information | Health mode | Health information | Address information |
|---|---|---|---|---|
| Chang Gung Memorial Hospital, Taipei | (121.5495, 25.0554) | Medical mode | Provide ER, cardiovascular outpatient services, etc. | 199 Tun Hua N. Rd., Taipei |
| Tokyo Fitness Club | (121.5482, 25.0519) | Exercising mode | Provide track mills, aerobatics courses, etc. | 10F, 337 Nanking E. Rd., Taipei |
| ... | ... | ... | ... | ... |

FIG. 3

HEALTH INFORMATION GUIDING SYSTEM AND METHOD THEREOF

BACKGROUND OF THE INVENTION

1. Field of Invention

The invention relates to a guiding system and the method thereof. In particular, the invention relates to a health information guiding system and the method thereof.

2. Related Art

In recent years, rapid developments in economy and industries have raised life standards. In addition to work, people start to pay more attention to their health. Health-related issues have become an important part of modern human life. With advances in electronic devices and software, the public can easily obtain biological detecting devices such as sphygmomanometers and scales to measure personal health parameters. Users can easily track their biological conditions in order to better monitor their health.

However, the health parameters collected from the biological detecting devices are mostly taken for the users to check whether there is any abnormality in health. If it has to wait until the user discovers the abnormality or even cannot realize that, the health data are basically useless. Moreover, the user may not know what to do with the health problem. For example, suppose a user knows that he is overweighed from the health data and may know that he has to do exercises to return to the normal weight. However, it is often the case that he does not know information about exercises, including the location of fitness centers, provided services, and address information. Another example is when the user has a very high systolic pressure and needs to go to hospital, but does not have medical care information. The above-mentioned problems are simply because existing technology cannot provide users with complete health care information.

In summary, the prior art has the problem of being able to provide users with more complete health care information. It is thus imperative to provide a solution for this.

SUMMARY OF THE INVENTION

In view of the foregoing, the invention discloses a health information guiding system that includes a location database, a receiving module, a coordinate analyzing module, a health analyzing module, a searching module, and an output module.

The location database stores a plurality of location data, each of which includes coordinate information, health mode, health information, and address information. The receiving module receives user information, location information, and health data. The coordinate analyzing module analyzes the coordinates of the location information to obtain coordinate ranges. The health analyzing module uses a set of analyzing conditions to analyze the health data, thereby obtaining a health mode. The searching module follows the coordinate ranges and the health mode to look for coordinate information that falls within the coordinate ranges and a location of the right health mode in the location database, thereby obtaining a target location and the corresponding health and address information. The output module outputs the target location and the corresponding health and address information according to the user information.

The disclosed health information guiding method includes the steps of: establishing a location database that stores a plurality of location data, each of which includes coordinate information, health mode, health information, and address information; receiving user information, location information, and health data; analyzing coordinates of the location information to obtain coordinate ranges; using a set of analyzing conditions to analyze the health data to obtain a health mode; searching in the location database for coordinate information that falls within the coordinate ranges and a location of the right health mode, thereby obtaining a target location and the corresponding health and address information; and outputting the target location and the corresponding health and address information according to the user information.

The disclosed system and method as described above differ from the prior art in that the invention analyzes the user's location information and health data to obtain the target location and to provide the user with the related health and address information.

Using the above-mentioned technique, the invention can increase the value of immediately using the health information.

BRIEF DESCRIPTION OF THE DRAWINGS

The invention will become more fully understood from the detailed description given herein below illustration only, and thus is not limitative of the present invention, and wherein:

FIGS. 3 to 5 are schematic views of the implementation of the disclosed health information guiding system.

DETAILED DESCRIPTION OF THE INVENTION

The present invention will be apparent from the following detailed description, which proceeds with reference to the accompanying drawings, wherein the same references relate to the same elements.

Figure 1:
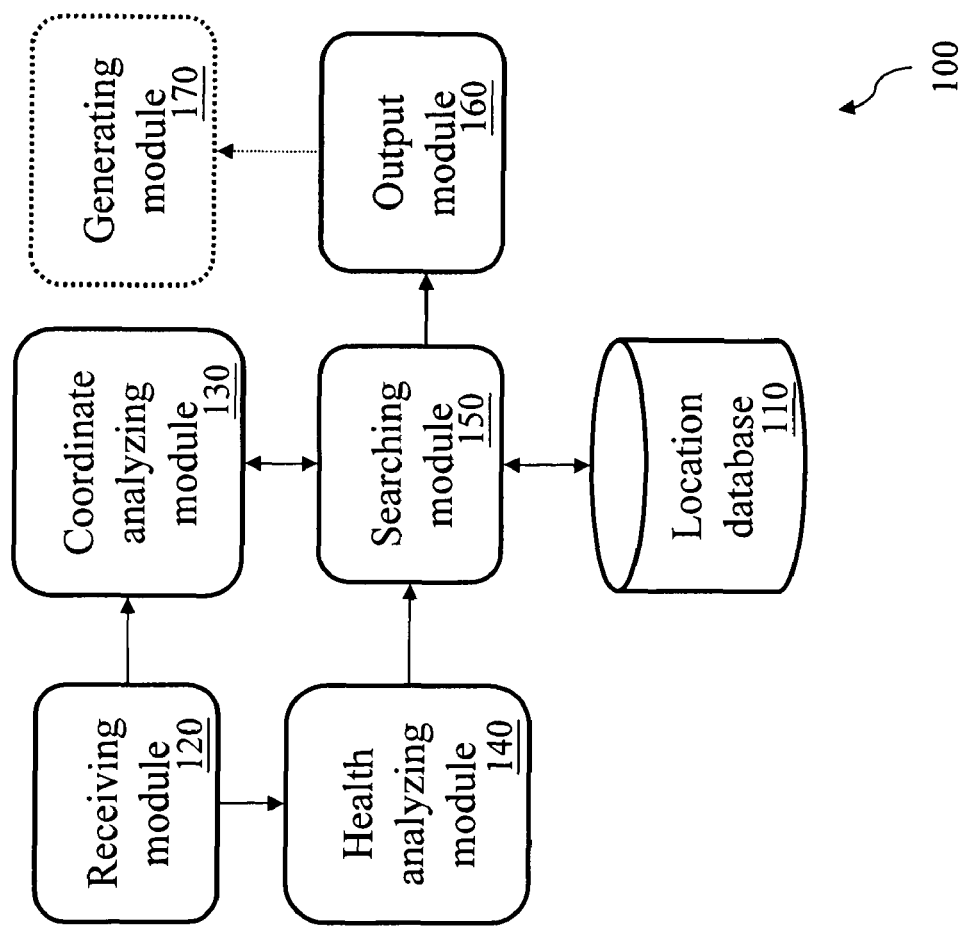
FIG. 1 is a block diagram of the disclosed health information guiding system.

Please refer FIG. 1, which is a block diagram of the disclosed health information guiding system. The health information guiding system 100 includes at least: a location database 110, a receiving module 120, a coordinate analyzing module 130, a health analyzing module 140, a searching module 150, and an output module 160.

The location database 110 stores a plurality of location data, each of which includes coordinate information, health mode, health information, and address information. The location data give physical locations that can provide health information, such as hospitals, clinics, drugstores, fitness equipment stores, etc. For example, the location data can be 'Chang Gung Memorial Hospital, Taipei', 'California Fitness Center', and 'San-Pu Fitness Equipment Store'. The coordinate information refers to the coordinates of each location. For example, the coordinate information for 'Chang Gung Memorial Hospital, Taipei' is '(121.5495, 25.0554)'. The health mode indicates the type of services provided at the location, whether it is a medical, fitness, or store mode. The health information gives the health services provided at the location. For example, the health information of the location data 'Chang Gung Memorial Hospital, Taipei' is 'emergency room, cardiovascular care, etc'. The address information refers to the address of the location. For example, the address information for 'Chang Gung Memorial Hospital, Taipei' is '199 Tun Hua N. Rd., Taipei'.

The receiving module 120 receives user information, location information, and health data. It should be noted that the user information is the information that can identify the user, such as the user's account, mobile phone number, home phone number, or E-mail address. The location information is entered by the user to indicate where he is located. For example, the user may enter the location information as '350 Nanking E. Rd., Sec. III, Taipei'. It should be noted that the health data include such data as body mass index (BMI), blood pressure, pulse, body temperature, or exercising state. The BMI is computed from the height and weight information entered by the user. The blood pressure, pulse and body temperature can be obtained from a sensor worn by the user. The exercising state can be the energy consumed by the user on fitness equipment. Therefore, the health data can be entered by the user or collected from sensors put on the user.

The coordinate analyzing module 130 analyzes the location information to obtain the coordinates thereof and thus coordinate ranges. That is, the coordinate analyzing module 130 analyzes the coordinates of the location information received by the receiving module 120 to obtain coordinate ranges. The coordinate ranges can be predetermined by the system, taking the coordinates of the location information as the central value and a fixed deviation around it. If there is no location data whose coordinate information falls within the coordinate ranges, the system enlarges the ranges until the coordinate information of some location data falls within the new coordinate ranges. Suppose in the above-mentioned example the location information is '350 Nanking Rd., Sec. III, Taipei' is analyzed to obtain its coordinates as '(121.5483, 25.0515)'. Taking '(121.5483, 25.0515)' as the central value, the coordinate ranges are determined to be, for example, '(121.5283~121.5683, 25.0315~25.0715)'.

The health analyzing module 140 uses a set of analyzing conditions to analyze the health data and obtain a health mode. It should be noted that the analyzing conditions are the medical standard ranges of the health data. As described above, the health data include the BMI, blood pressure, pulse, body temperature, or exercising state. Take the BMI as an example. The analyzing condition can be in accord with the standard set by the World Health Organization (WHO): fat when the BMI≧25, overweighed when 23≦BMI<24.9, normal when 18.5<BMI≦22.9, etc. Therefore, the analyzing conditions can be 'normal when the BMI<23' and 'abnormal when the BMI≧23'. For example, if the BMI in the health data of the user is '24', then the health analyzing module 140 determines it to be 'abnormal'. The health mode is thus determined as the 'exercise mode', which suggests that the user work out in a fitness center in order for the BMI to return to its normal value. It should be noted that in the above-mentioned example, the health modes include a medical mode, an exercise mode, and a store mode. By default, the system selects the exercising mode when the BMI is abnormal. If the blood pressure, pulse, or temperature is abnormal as well, then it selects the medical mode. If the exercising state is abnormal, then it selects the store mode. In other examples, the system can be set such that it selects the medical mode when the BMI is abnormal and the exercising mode when the exercising state is abnormal. The invention is not limited by such examples. As long as the system has a predetermined health mode for the health data analysis result, it is within the scope of the invention.

The searching module 150 searches in the location database 110 for locations whose coordinate information falls within the coordinate ranges and whose health mode matches with the system's selection. It extracts the corresponding health and address information. That is, the searching module 150 uses the coordinate ranges obtained by the coordinate analyzing module 130 and the health mode obtained by the health analyzing module 140 to search for location data in the location database. The only criteria are that the coordinate information of the location data has to fall within the coordinate ranges and that the health mode is the same as that obtained by the health analyzing module 140. It should be noted that if there is no location data whose coordinate information falls inside the coordinate ranges, the coordinate analyzing module 130 enlarges them to obtain new coordinate ranges until the coordinate information of some location data falls into the ranges. The location data satisfying the above-mentioned criteria give at least one target location. The system then extracts the health and address information of the target location. Following the above-mentioned example, suppose the coordinate ranges are '(121.5283~121.5683, 25.0315~25.0715)' and the health mode is the 'medical mode'. The searching module finds that the location data 'Chang Gung Memorial Hospital, Taipei' has the coordinate information '(121.5495, 25.0554)' falling into the coordinate ranges '(121.5283~121.5683, 25.0315~25.0715)' and its health mode matches too. So 'Chang Gung Memorial Hospital, Taipei' becomes a target location. The system then provides the corresponding health information, such as 'please go to ER for emergency' and 'please go to cardiovascular medicine'. The system also provides the corresponding address information, such as '350 Nanking E. Rd., Sec. III, Taipei'.

The output module 160 outputs the target location and the corresponding health and address information according to the user information. It should be noted that the output module 160 uses a web interface, E-mail message, mobile phone short message, or telephone voice message according to the user information to output the target location and the corresponding health and address information. Since the user information includes the user account, mobile phone number, home phone number, or E-mail address, the system can directly present the target location and the corresponding health and address information on a web page. It can also send the target location and the corresponding health and address information through a mobile phone short message using the mobile phone number. Or it can send the target location and the corresponding health and address information via E-mail using the E-mail address.

Moreover, the health information guiding system 100 can further include a generating module 170 that generates a reference map and direction based on the location information, the target location, and the corresponding traffic information. The user can then follow the reference map and direction to go to the target location.

Through the operation of the above-mentioned health information guiding system, the user can obtain more complete health information by analyzing the location information and the health data of the user and providing the relevant health and address information.

The following paragraphs describe the procedure of the disclosed method and disclose an explicit embodiment. However, this particular embodiment should not be used to limit the scope of the invention defined in the claims.

Figure 2:
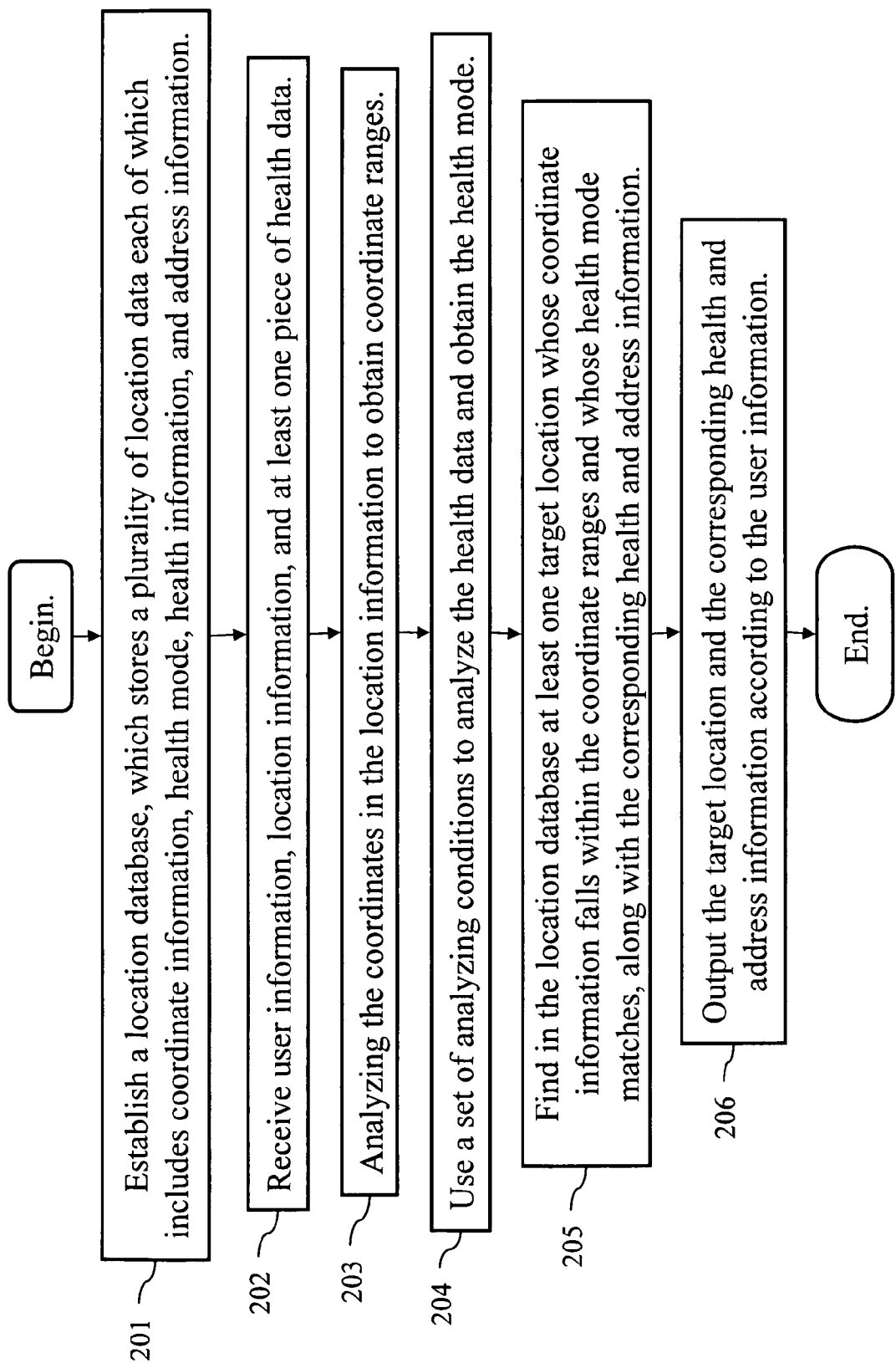
FIG. 2 is a flow chart of the disclosed health information guiding method.
Figure 4:
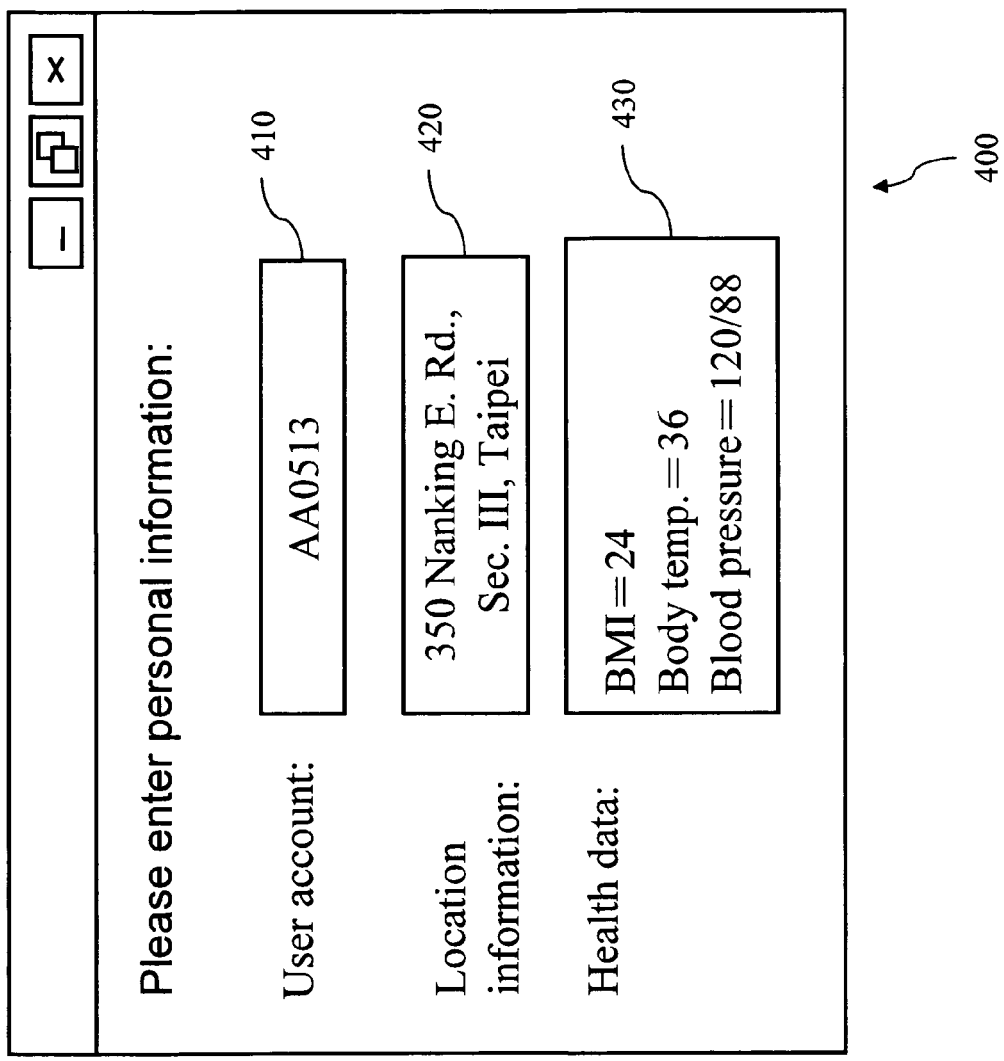
Figure 5:
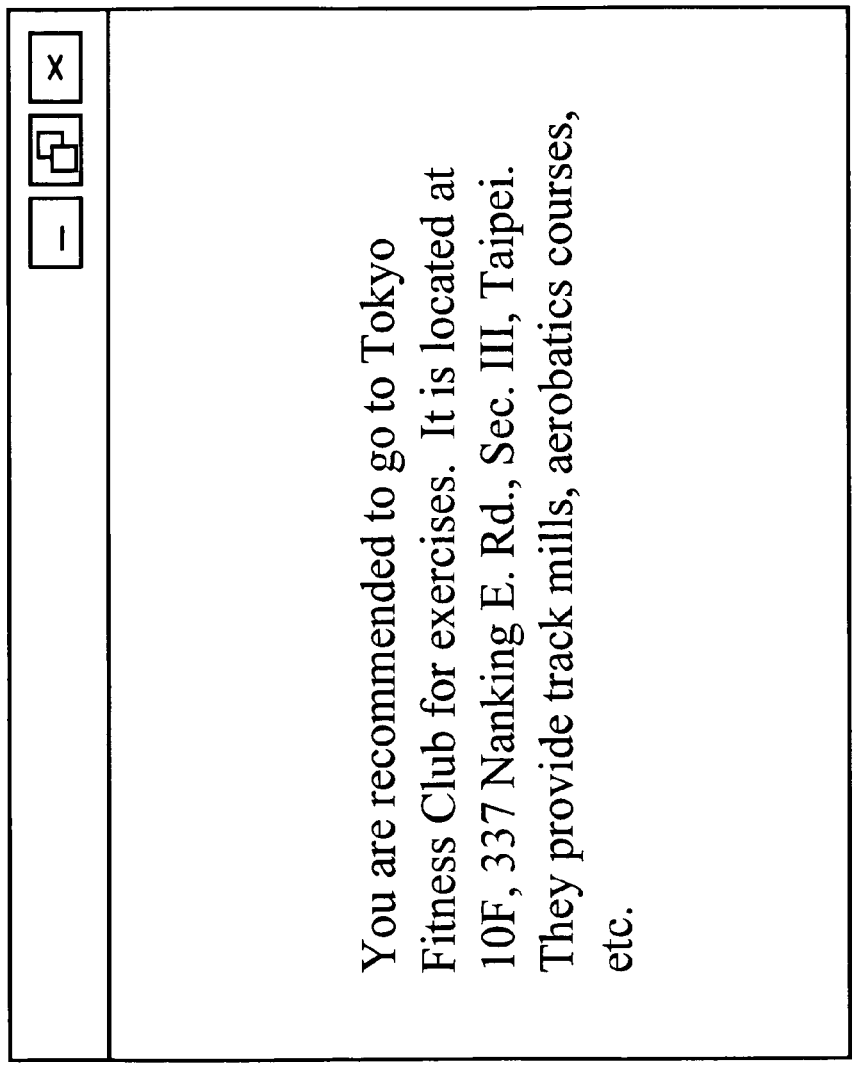

FIG. 2 is a flowchart of the disclosed health information guiding method. FIGS. 3 to 5 are schematic views showing how the disclosed system is implemented. Please refer to FIGS. 2 to 5 for the following explanation.

With reference to FIG. 3, the health information guiding system 100 provides the user with health information browsing and guidance. First, the health information guiding system 100 first establishes a location database 300. The location database 300 stores several location data 310, such as 'Chang Gung Memorial Hospital, Taipei' and 'Tokyo Fitness Club'. Each piece of location data 310 has coordinate information 320, health mode 330, health information 340, and address information 350. The coordinate information 320 can be, for example, '(121.5495, 25.0554)' and '(121.5482, 25.0519)'. The health mode 330 can be, for example, the 'medical mode' and 'exercising mode'. The health information 340 can be, for example, 'provide ER, cardiovascular outpatient services, etc' and 'provide track mills, aerobatics course, etc'. The address information 350 can be, for example, '199 Tun Hua N. Rd., Taipei' and '10F, 337 Nanking E. Rd., Sec. III, Taipei'. (Step 201)

Please refer to FIG. 4. The user information input interface 400 includes a user account input field 410, a location information input field 420, and a health data input field 430. The user uses the user account input field 410 in the user information input interface 400 to enter a user account 'AA0513', the location information input field 420 to enter '350 Nanking E. Rd., Sec. III, Taipei', and the health data input field 430 to enter the health data: 'BMI=24, temperature=36, and blood pressure=120/88'. The health information guiding system 100 uses the user account 'AA0513' to verify whether the user is a member, thereby determining whether to provide the services. After the user enters all the information, the health information guiding system 100 receives the user account 'AA0513', the location information '350 Nanking E. Rd., Sec. III, Taipei', and the health data 'BMI=24, temperature=36, and blood pressure=120/88'. (Step 202)

Afterwards, the health information guiding system 100 analyzes the location information '350 Nanking E. Rd., Sec. III, Taipei' to have the coordinate '(121.5483, 25.0515)', according to which the coordinate ranges '(121.5283~121.5683, 25.0315~25.0715)' are obtained (step 203). Furthermore, according to the analyzing conditions 'normal if the BMI<23, abnormal and exercising mode when BMI □ 23; normal if the body temperature<38, abnormal and medical mode if the body temperature □ 38; normal if the blood pressure<130/90, abnormal and medical mode if the blood pressure □130/90'. After analyzing the health data 'BMI=24, temperature=36, and blood pressure=120/88', the health mode 330 is determined to be the 'exercising mode' (step 204). The above-mentioned embodiment is only one example of the invention. In other embodiments, the medical mode and the exercising mode may be simultaneously suggested. In this case, the health information guiding system 100 searches in the location database 300 the location data that satisfy the medical mode and the exercising mode. However, the invention is not limited to only these examples.

The health information guiding system 100 uses the coordinate ranges '(121.5283~121.5683, 25.0315~25.0715)' and the health mode 330 'exercising mode' to find in the location database 300 that the location data 310 whose coordinate information 320 falls in the coordinate ranges '(121.5283~121.5683, 25.0315~25.0715)' and whose health mode 330 matches is 'Tokyo Fitness Club'. It is the target location. The corresponding health information 340 includes 'provide track mills, aerobatic course, etc'. The corresponding address information 350 is then '10F, 337 Nanking E. Rd., Sec. III, Taipei'. (Step 205)

Please refer to FIG. 5. The health information guiding system 100 integrates the target location 'Tokyo Fitness Club', the health information 340 'provide track mills, acrobatic course, etc', and the address information 350 '1° F., 337 Nanking E. Rd., Sec. III, Taipei' and show them in the health information guiding display interface 500. (Step 206)

In summary, the invention differs from the prior art in that it analyzes the user's location information and health data to obtain a target location. It further provides the user with the health information and the address information. Using the invention, the user can obtain more complete health information. This increases the value of immediately using the health information.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A health information guiding system, comprising:
   a location database, which stores a plurality of location data each of which has coordinate information, health mode, health information, and address information;
   a receiving module, which receives user information, location information, and at least one piece of health data;
   a coordinate analyzing module, which analyzes the coordinates of the location information to obtain coordinate ranges;
   a health analyzing module, which uses a set of analyzing conditions to analyze the health data to obtain a health mode;
   a searching module, which uses the coordinate ranges and the health mode to find in the location database at least one target location whose coordinate information falls within the coordinate ranges and whose health mode matches, thereby obtaining the corresponding health and address information; and
   an output module, which outputs the target location and the corresponding health and address information according to the user information.

2. The health information guiding system of claim 1 further comprising a generating module for generating a reference map and at least one piece of traffic information according to the location information, the target location, and the corresponding address information.

3. The health information guiding system of claim 1, wherein the user information includes the user account, mobile phone number, home phone number, and E-mail address.

4. The health information guiding system of claim 1, wherein the health data include the body mass index (BMI), blood pressure, pulse, body temperature, and exercising state.

5. The health information guiding system of claim 4, wherein the analyzing conditions are the medical standard ranges of the health data.

6. The health information guiding system of claim 1, wherein the output module outputs the target location and the corresponding health and address information through a web interface, E-mail messages, mobile phone short messages, and home phone voice messages according to the user information.

7. A health information guiding method, comprising the steps of:
   establishing a location database, which stores a plurality of location data each of which includes coordinate information, health mode, health information, and address information;
   receiving user information, location information, and at least one piece of health data;
   analyzing the coordinates in the location information to obtain coordinate ranges;
   using a set of analyzing conditions to analyze the health data and obtain the health mode;
   finding in the location database at least one target location whose coordinate information falls within the coordinate ranges and whose health mode matches, along with the corresponding health and address information; and outputting the target location and the corresponding health and address information according to the user information.

8. The health information guiding method of claim 7 further comprising the step of generating a reference map and at least one piece of traffic information according to the location information, the target location, and the corresponding address information.

9. The health information guiding method of claim 7, wherein the user information includes the user account, mobile phone number, home phone number, and E-mail address.

10. The health information guiding method of claim 7, wherein the health data include the BMI, blood pressure, pulse, body temperature, and exercising state.

11. The health information guiding method of claim 10, wherein the analyzing conditions are the medical standard ranges of the health data.

12. The health information guiding method of claim 7, wherein the step of outputting the target location and the corresponding health and address information according to the user information is done via a web interface, E-mail messages, mobile phone short messages, and home phone voice messages.

* * * * *